(12) United States Patent
Liu et al.

(10) Patent No.: US 7,244,724 B2
(45) Date of Patent: Jul. 17, 2007

(54) PYRROLOBENZODIAZEPINES

(75) Inventors: Paul S. Liu, Chevy Chase, MD (US); B. Rao Vishnuvajjala, Rockville, MD (US); Kenneth M. Snader, Vero Beach, FL (US); David E. Thurston, Foreham (GB); Philip Howard, St. Albans (GB); Stephen Gregson, London (GB)

(73) Assignees: United States of America, Represented by the Secretary, Department of Health and Human Services, Washington, DC (US); Spirogen, Ltd., London (GB)

( * ) Notice: Subject to any disclaimer, the term of this patent is extended or adjusted under 35 U.S.C. 154(b) by 0 days.

(21) Appl. No.: 11/129,207

(22) Filed: May 13, 2005

(65) Prior Publication Data

US 2006/0270661 A1    Nov. 30, 2006

Related U.S. Application Data

(63) Continuation of application No. PCT/GB04/04497, filed on Oct. 22, 2004.

(60) Provisional application No. 60/513,751, filed on Oct. 22, 2003.

(51) Int. Cl.
C07D 403/12 (2006.01)
A61K 31/5517 (2006.01)

(52) U.S. Cl. .................... 514/220; 540/496

(58) Field of Classification Search ............... 540/496; 514/220
See application file for complete search history.

(56) References Cited

U.S. PATENT DOCUMENTS

| 4,464,467 A | 8/1984 | Hatori et al. |
| 4,508,647 A | 4/1985 | Hatori et al. |
| 2003/0120069 A1 | 6/2003 | Thurston et al. |

FOREIGN PATENT DOCUMENTS

| EP | 1 193 270 B1 | 5/2003 |
| JP | 58180487 | 10/1983 |
| WO | WO 93/18045 A1 | 9/1993 |
| WO | WO 00/12508 A2 | 3/2000 |

OTHER PUBLICATIONS

Alley et al., *Proc. Amer. Cancer Res.*, 43, (#315), 63 (2002).
Berge et al., *J. Pharm. Sci.*, 66(1), 1-19 (1977).
Bose et al., *Tetrahedron*, 48(4), 751-758 (1992).
Gregson et al., *Chem. Commun.*, 9, 797-798 (1999).
Gregson et al., *J. Med. Chem.*, 44(5), 737-748 (2001).
Gregson et al., *J. Med. Chem.*, 47(5), 1161-1174 (2004).
Hartley et al., *Proc. Amer. Assoc. Cancer Res.*, 43, (#2432), 489 (2002).
Hurley et al., *Acc. Chem. Res.*, 19, 230-237 (1986).
Kohn, *Antibiotics*, 3, 3-11 (1975).
Leimgruber et al., *J. Am. Chem. Soc.*, 87, 5791-5793 (1965).
Leimgruber et al., *J. Am. Chem. Soc.*, 87, 5793-5795 (1965).
Mountzouris et al., *J. Med. Chem.*, 37(19), 3132-3140 (1994).
Smellie et al., *Br. J. Cancer*, 70, 48-53 (1994).
Thurston et al., *Chem. Rev.*, 1994, 433-465 (1994).
Walton et al., *Cancer Chemother. Pharmacol.*, 38, 431-438 (1996).
Arima et al., *J. Antibiotics*, 25(8), 437-444 (1972).
Hara et al., *J. Antibiotics*, 41(5), 702-704 (1988).
Hochlowski et al., *J. Antibiotics*, 40(2), 145-148 (1987).
Itoh et al., *J. Antibiotics*, 41(9), 1281-1284 (1988).
Konishi et al., *J. Antibiotics.*, 37(3), 200-206 (1984).
Kuminoto et al., *J. Antibiotics*, 33(6), 665-667 (1980).
Langley et al., *J. Org. Chem.*, 52(1), 91-97 (1987).
Leber et al., *J. Am. Chem. Soc.*, 110(9), 2992-2993 (1988).
Sagnou et al., *Bioorg. Med. Chem. Lett.*, 10, 2083-2086 (2000).
Shimizu et al., *J. Antibiotics*, 35(8), 972-978 (1982).
Takeuchi et al., *J. Antibiotics*, 29(1), 93-96 (1976).
Thurston et al., *Chem. Brit.*, 26, 767-772 (1990).
Thurston et al., *J. Org. Chem.*, 61(23), 8141-8147 (1996).
Tsunakawa et al., *J. Antibiotics*, 41, 1366-1373 (1988).
Turner et al., 37th Midwest Regional Meeting of the American Chemical Society, Abstract, Oct. 23-25, 2002.

*Primary Examiner*—Bruck Kifle
(74) *Attorney, Agent, or Firm*—Leydig, Voit & Mayer, Ltd.

(57) ABSTRACT

A compound of formula I:

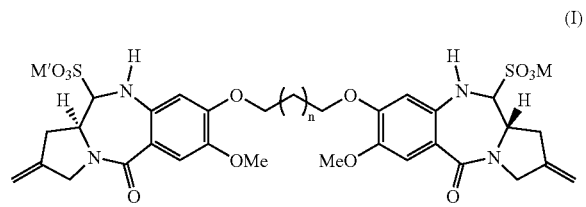

(I)

or solvate thereof, wherein n is 1 to 10, and M and M' are independently selected from monovalent pharmaceutically acceptable cations, or together represent a divalent pharmaceutically acceptable cation.

14 Claims, No Drawings

PYRROLOBENZODIAZEPINES

This application is a continuation of PCT/GB04/04497, filed Oct. 22, 2004, which claims the benefit of U.S. Provisional Patent Application No. 60/513,751, filed Oct. 23, 2003.

The present invention relates to bisulphite derivatives of SJG-136 and DRG-16, and analogues thereof.

BACKGROUND OF THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793–5795 (1965); Leimgruber, et al., *J. Am. Chem. Soc.*, 87, 5791–5793 (1965)). Since then, a number of naturally occurring PBDs have been reported, and over 10 synthetic routes have been developed to a variety of analogues (Thurston, et al., *Chem. Rev.* 1994, 433–465 (1994)). PBDs are of the general structure:

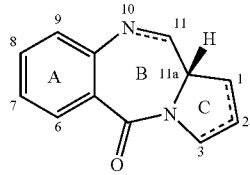

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity within the minor groove of B-form DNA, leading to a snug fit at the binding site (Kohn, In *Antibiotics III*. Springer-Verlag, New York, pp. 3–11 (1975); Hurley and Needham-VanDevanter, *Acc. Chem. Res.*, 19, 230–237 (1986)). Their ability to form an adduct in the minor groove, enables them to interfere with DNA processing, hence their use as antitumour agents.

In WO 00/12508, some of the present inventors disclosed the following compound (SJG-136, Compound 80):

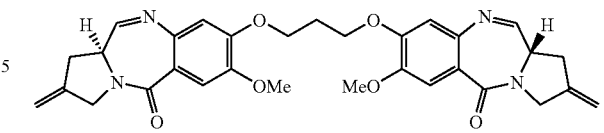

This compound is also disclosed in Gregson, S. J., et al., *Chem. Commun.*, 1999, 797–798. It has entered Phase I clinical trials in the UK and is likely to enter Phase I clinical trials in the US shortly.

One difficulty that this compound presents in formulation is that in water it converts to the di-carbinolamine form:

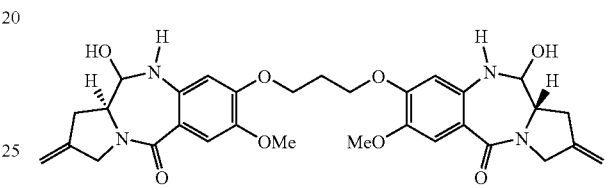

and when isolated often exists as a mixture of the imine, mono-carbinolamine and the di-carbinolamine forms. Furthermore, if the compound is isolated as a solid with a mixture of these three forms, the balance between them may change over time. Although this does not pose a problem for administration of the compound, it can provide difficulties in accurately assessing the amount of active substance in a given amount of powder.

SJG-136 does not appear to exhibit the cardiotoxicity that has been associated with pyrrolobenzodiazepines in the past.

Also disclosed in WO 00/12508, is the following compound (DRG-16, Compound 218):

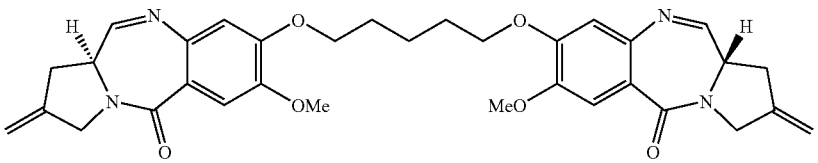

This compound is also disclosed in Gregson, S. J., et al., *J. Med. Chem.*, 2004, 1161–1174, in which it is shown to have similar properties to SJG-136.

DISCLOSURE OF THE INVENTION

The present inventors have surprisingly discovered that the bis-bisulphites of SJG-136 and DRG-16, and analogues thereof, appear to be resistant to the interconversion described above, but retain activity, and therefore are suitable for formulation.

Accordingly, in a first aspect, the invention comprises a compound of formula I:

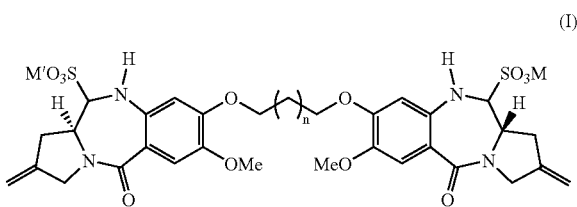

(I)

or solvate thereof, wherein n is 1 to 10, and M and M' are independently selected from monovalent pharmaceutically acceptable cations, or together represent a divalent pharmaceutically acceptable cation.

When n is 1, the compound is of formula:

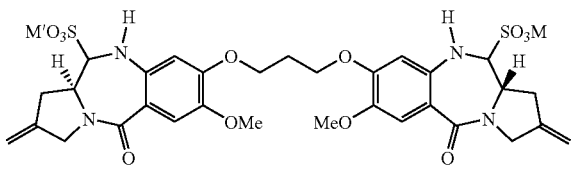

When n is 3, the compound is of formula:

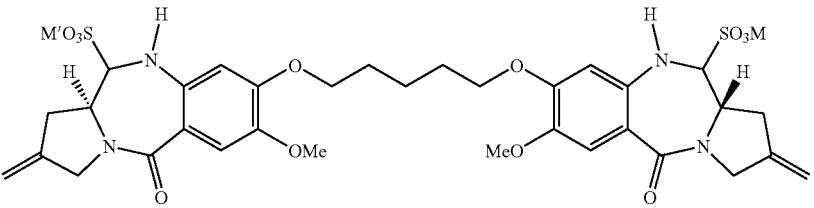

It is preferred that n is 1, 3, 6, 7 or 8, with 1 or 3 being more preferred.

In a second aspect, the invention comprises the synthesis of a compound of formula I or solvate thereof.

In a third aspect, the invention comprises a compound of formula I or solvate thereof, for use in a method of therapy.

In a fourth aspect, the invention comprises a pharmaceutical composition comprising a compound of formula I or solvate thereof, and a pharmaceutically acceptable excipient.

In a fifth aspect, the invention comprises the use of a compound of formula I or solvate thereof, in the manufacture of a medicament for the treatment of a gene-based disease.

In a sixth aspect, the invention comprises a method for the treatment of a gene-based disease, comprising administering to a subject suffering from a gene-based disease a therapeutically-effective amount of a compound of formula I or solvate thereof.

DEFINITIONS

Pharmaceutically Acceptable Cations

Examples of pharmaceutically acceptable monovalent and divalent cations are discussed in Berge, et al., *J. Pharm. Sci.*, 66, 1–19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Gene-based Diseases

Gene-based diseases include, and are preferably, proliferative diseases, and also include Alzheimer's disease and bacterial, parasitic and viral infections. Any condition which may be treated by the regulation of gene expression may be treated the compounds of the present invention.

Proliferative Diseases

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Karposi's sarcoma, melanoma), leukaemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Methods of Treatment

As described above, the present invention provides the use of a compound of formula I in a method of therapy. Also provided is a method of treatment, comprising administering to a subject in need of treatment a therapeutically-effective amount of a compound of formula I, preferably in the form of a pharmaceutical composition, which is the third aspect of the present invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs); surgery; and radiation therapy.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes other Forms

Included in the above are the ionic forms of the compound of formula I.

In particular, a reference to the bisulphite group (—SO$_3$M) also includes the anionic form (—SO$_3^-$), or solvate thereof, as well as conventional protected forms.

Isomers and Solvates

Certain compounds may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of the present invention have the following stereochemistry at the C11 position:

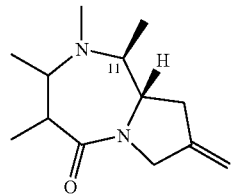

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

General Synthetic Routes

The compounds of formula I may be made directly from SJG-136, whose synthesis by two alternative routes is described in WO 00/12508, or from DRG-16, whose synthesis is also described in WO 00/12508, or their analogues, as appropriate.

The synthesis of compound I involves the addition of a solution of the appropriate bisulphite salt to a solution of SJG-136 or DRG-16, or their analogues, which is usually followed by a purification step.

Further Preferences

It is preferred that M and M' are the same and that there are alkali metal ions, most preferably Na$^+$.

It is preferred that the compound of formula I is present in purified or isolated form. For the purposes of the present invention, the term "isolated" as used herein is defined as having been removed from its natural environment. The term "purified" as used herein refers to having been increased in purity, wherein "purity" is a relative term, and not to be construed as absolute purity. The terms "isolated" and "purified" do not necessarily imply 100% or complete isolation or purity. Rather, there are varying degrees of isolation or purity of which one of ordinary skill in the art recognizes as having a potential benefit or prophylactic or therapeutic effect. In this regard, the compounds of the present invention can be of any level of isolation or purity. Preferably, the compound of formula I is substantially isolated or substantially pure, such that the compounds are substantially free of any impurities or any materials or agents that, for example, interfere with the activity of the compounds or make the compounds toxic.

Further preference are that the compound of formula I is substantially free of any of the parent compound, e.g. SJG-136 or DRG-16 or their analogues, wherein the amount of the parent compound is preferably less than 5% by weight, and more preferably-less than 1%, 0.1% or even 0.01% by weight.

As regards the stereochemistry of the compound of formula I, it is preferred that it comprises at least 70%, 80%, 90%, 95% or 99% in the preferred configuration for C11 as discussed above.

EXAMPLES

Example 1

Synthesis of 1,1'[[(Propane-1,3-diyl)dioxy]bis (11aS)-11-sulpho-7-methoxy-2-methylidene-1,2,3, 10,11,11a-hexahydro-5H-pyrrolo[2,1-c][1,4-benzo-diazepin-5-one]] sodium salt (SJG-720)

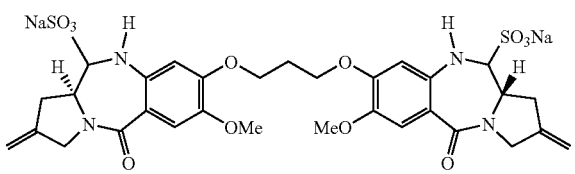

A solution of sodium bisulphite (13.2 mg, 0.127 mmol) in water (5.2 mL) was added to a stirred solution of SJG-136 (35.19 mg, 63.3 μmol) in dichloromethane (2.5 mL, Aldrich sure seal grade). The reaction mixture was allowed to stir vigorously for 24 hours, after which time the organic and aqueous layers were separated. TLC analysis (eluent-95:5 v/v CHCl$_3$/MeOH) of the aqueous phase revealed absence of SJG-136 (R$_f$~0.3) and presence of baseline material with strong uv absorption. The aqueous layer was lyophilised to provide the bisulphite adduct SJG-720 as a lightweight white solid (40.88 mg, 85%). Mpt. 213–216° C. $[\alpha]^{29}_D$+126.2° (c=0.0317 MeOH)

Example 2

Synthesis of 1,1'[[(Pentane-1,3-diyl)dioxy]bis (11aS)-11-sulpho-7-methoxy-2-methylidene-1,2,3, 10,11,11a-hexahydro-5H-pyrrolo[2,1-c][1,4-benzo-diazepin-5-one]] sodium salt (SJG-738)

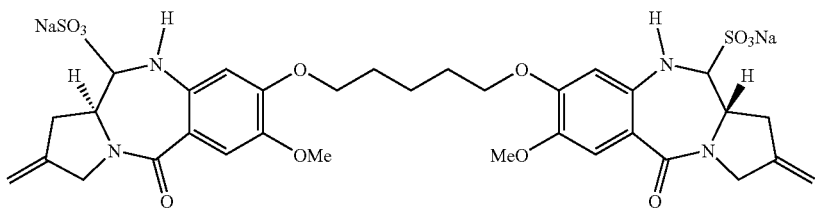

A solution of sodium bisulphite (16.46 mg, 0.158 mmol) in water (3.0 mL) was added to a stirred solution of DRG-16 (46.2 mg, 79.1 μmol) in dichloromethane (1.5 mL, Aldrich sure seal grade). The reaction mixture was allowed to stir vigorously for 22 hours, after which time the organic and aqueous layers were separated. TLC analysis (eluent-95:5 v/v CHCl$_3$/MeOH) of the aqueous phase revealed absence of DRG-16 (R$_f$~0.3) and presence of baseline material with strong uv absorption. The aqueous layer was lyophilised to provide the bisulphite adduct SJG-738 as a lightweight white solid (47.95 mg, 77%). Mpt. 203–204° C. $[\alpha]^{27}_D$+117.6° (c=0.0425 MeOH).

Further Studies

All NMR experiments were performed using a Bruker Avance 400 MHz NMR spectrophotometer. NMR solvents were purchased from Goss Scientific.

Techniques

One Dimensional NMR Experiments (Studies 1, 2 and 3)

Samples of SJG-720 (~3 mg) were dissolved in d$_6$-DMSO, D$_2$O and d$_4$-MeOH (Cambridge Isotopes) and transferred to separate NMR tubes (Wilmad, 5 mm). $^1$H NMR spectra were obtained on a Bruker Avance 400 MHz NMR spectrophotometer (typically 64 scans). $^{13}$C and DEPT (Distortionless Enhancement through Polarized Transfer) experiments were performed on these samples using the same instrument at the appropriate field strength (100 MHz).

Study 4

NMR spectra were recorded, as described above, after the following time intervals:

d$_6$-DMSO, 1 hr, 8 days.
D$_2$O, 3 hrs, 8 days.
d$_4$-MeOH, 10 minutes, 3 days.

Additional Studies

Standard two dimensional NMR techniques COSY (COrrelated SpectroscopY) and HMQC (Heteronuclear Multiple Quantum Coherence) were employed to assign NMR shifts. Comparative NMR spectra for SJG-136 were obtained on a Bruker Avance 500 MHz NMR instrument.

Details of Studies

Study 1: NMR Studies in $d_6$-DMSO

A solution of SJG-720 in $d_6$-DMSO was analysed by $^1$H and $^{13}$C NMR spectroscopy and signals assigned (see below) with the aid of additional NMR experiments (DEPT, COSY and HMQC). Without wishing to be bound by theory, initial observations suggest that the molecule exists as predominantly one diastereoisomer and the presence of the N10-C11 imine form is not detected. Key signals in the $^1$H NMR include N10-H (δ 5.06 ppm), H11 (δ 3.74 ppm, d, J=10.5 Hz) and a broad singlet at δ 5.06 ppm corresponding to C2=CH$_2$. The $^{13}$C NMR DEPT spectrum also exhibits diagnostic signals such as C11 (δ 78.8 ppm) and the intact C2=CH$_2$ (δ 107.8 ppm).

Study 3: NMR Studies in $d_4$-MeOH

NMR experiments were also performed on a solution of SJG-720 in $d_4$-MeOH. Without wishing to be bound by theory, the $^1$H NMR spectrum shows the presence of only one diastereoisomer with signals for H11, H$_{11}$a, H3 and OCH$_2$CH$_2$CH$_2$O overlapping with each other. However, HMQC and COSY experiments were able to assist in identifying H11 (δ 4.13 ppm, d, J=10.7 Hz). Other key signals visible in the spectrum include H6 (δ 7.15 ppm), H9 (δ 6.72 ppm), C2=CH$_2$ (δ 5.16, 5.18 ppm), OCH$_3$ (δ ⁻ 3.83 ppm), H1 (δ 3.08 ppm, d, J=16 Hz and δ 3.07–2.98 ppm) and OCH$_2$CH$_2$CH$_2$O (p, δ 2.33 ppm, J=6.1 Hz). The exchangeable NH signal is absent from this spectrum. Key signals in the $^1$H NMR spectrum correlate (HMQC) with the corresponding carbon signals in the $^{13}$C DEPT NMR: C6 (δ 113.6 ppm), C2=CH$_2$ (δ 109.4 ppm), C9 (δ 108.5 ppm), C11 (δ 81.5 ppm), OCH$_2$CH$_2$CH$_2$O (δ 66.6 ppm), C11a (δ 58.9 ppm), OCH$_3$ (δ 57.0 ppm), C3 (δ 51.6 ppm), C1 (δ 37.1 ppm) and OCH$_2$CH$_2$CH$_2$O (δ30.2 ppm).

$^1$H NMR

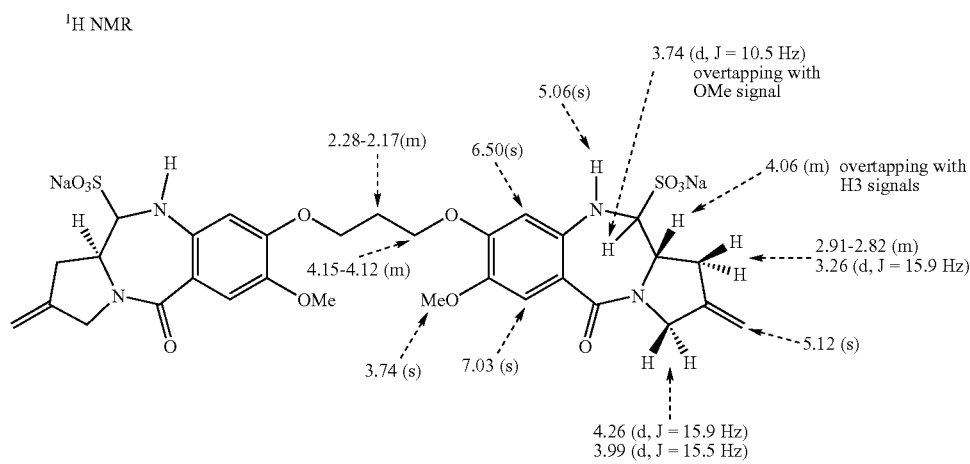

$^{13}$C NMR

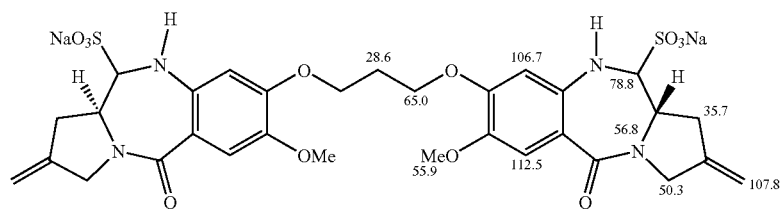

Quat Carbon signals: 167.0, 150.8, 143.8, 143.0, 140.1 & 116.6

Assignment of NMR Signals for SJG-720 in $d_6$-DMSO.

Study 2: NMR Studies in D$_2$O

A solution of SJG-720 in D$_2$O was analysed by $^1$H NMR spectroscopy and key signals assigned with the aid of a COSY experiment. Although the spectrum appears relatively clean and shows, without wishing to be bound by theory, the presence of predominantly one diastereoisomer a number of key signals overlap with each other, signals for H11, H11a, H3 and OCH$_2$CH$_2$CH$_2$O all resonate between δ 4.12–4.45 ppm. Clearly resolved signals include H6 (δ 7.18 ppm), H9 (δ 6.78 ppm), C2=CH$_2$ (δ 5.27 ppm), OCH$_3$ (δ 3.85 ppm), H1 (δ 3.08 ppm) and OCH$_2$CH$_2$CH$_2$O (distorted p, δ 2.36 ppm). The exchangeable NH signal is absent from this spectrum.

Study 4: Stability in $d_6$-DMSO, $d_4$-MeOH and D$_2$O

As discussed above, PBDs exist in three interconvertable forms around the N10-C11 bond and this is shown for SJG-136:

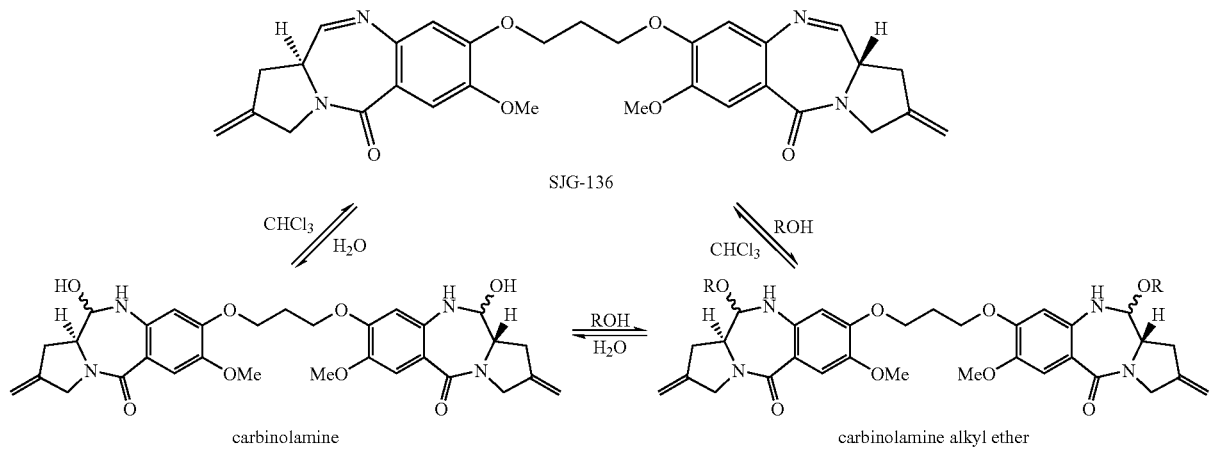

SJG-136 carbinolamine carbinolamine alkyl ether

NMR experiments were carried out on SJG-136 in its carbinolamine forms. The carbinolamine forms are revert to the imine form immediately if analysed in either CDCl$_3$ or CD$_3$CN. However, strong signals corresponding to the kinetic and thermodynamic carbinolamine forms can be observed when the sample is analysed in d$_6$-DMSO. These gradually disappear from the spectra over a period of about 24 hours when the imine form becomes the predominant species.

Samples of the bisulphite adduct SJG-720 dissolved in d$_6$-DMSO and D$_2$O were stored at room temperature for over a period of 7 days and then analysed by $^1$H NMR spectroscopy. In the case of the D$_2$O solution the spectrum remained unchanged from day 1, i.e. no appreciable hydrolysis had occurred. Similarly, the spectrum obtained from prolonged storage of the sample in d$_6$-DMSO showed the complete absence of parent imine SJG-136 signals. In addition, a sample of SJG-720 stored at room temperature in d$_4$-MeOH for over 3 days was also analysed by $^1$H NMR. Again, interconversion to the carbinolamine methyl ether from was not observed by NMR.

Study 5: Stereochemistry at C11

The NMR studies described above appear to have determined that the PBD bisulphite adducts are formed in a stereocontrolled fashion to afford almost exclusively a single diastereomeric product.

NMR studies of SJG-720 in d$_4$-MeOH reveal a coupling constant of ~10 Hz between the vicinal protons H11 and H11a. This coupling constant is consistent with a large dihedral angle and trans stereochemistry between the vicinal protons. It therefore appears that SJG-720 possesses the absolute stereochemistry shown below:

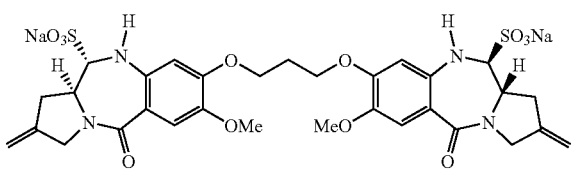

Study 6: NMR spectra of SJG-738

$^1$H-NMR (400 MHz, d$_6$ DMSO) δ 7.00(s, 2H), 6.43 (s, 2H), 5.08 (s, 4H), 5.04 (s, 2H), 4.22 (d, J=15.78 Hz), 4.03–3.89 (m, 8H), 3.71 (s, 6H), 3.71 (d, J=10.5 Hz, 2H), 3.23 (d, 15.7 Hz, 2H), 2.87–2.81 (dd, J=15.8, 9.1 Hz, 2H), 1.82 (p, J=7.3 Hz, 4H), 1.63–1.54 (m, 2H).

$^{13}$C NMR (100 MHz, d$_6$ DMSO) δ 167.1, 151.1, 143.8, 142.9, 140.1, 116.3, 112.4, 107.8, 106.3, 78.8, 68.0, 56.7, 55.9, 50.3, 35.7, 28.4, 22.2.

Biological Results

K562 Assay

An initial stock of compound (in 0.006% DMSO) was used to generate a 1:3 dilution series ranging from 600 nM to 30 pM be the sequential addition of 40 μL compound to 80 μL of solvent (0.006% DMSO in sterile H$_2$O). 10 μL of each point of the dilution range was transferred to a 96 well assay plate (Nunc, Cat. No. 163320) to generate four replica points per compound concentration. K562 human chronic myeloid leukaemia cells were maintained in RPM1 1640 medium supplemented with 10% foetal calf serum and 2 mM glutamine at 37° C. in a humidified atmosphere containing 5% CO$_2$. 190 μL of a 5×10$^4$ cell solution was added to each well of the assay plate using a Matrix Wellmate (Apogent Discoveries), resulting in a total of 9.5×10$^3$ cells/well. Working compound concentrations therefore ranged from 30 nM to 1.5 pM. Plates were then kept in the dark at 37° C. in a humidified atmosphere containing 5% CO$_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 25 μL of MTT solution (5 mg/mL in phosphate-buffered saline) was added to each well and the plates further incubated for 4 hours. The bulk of the medium was then pipetted from the cell pellet leaving 10–20 μL per well. DMSO (200 μL) was added to each well and the samples agitated to ensure complete mixing. The optical density was then read at a wavelength of 540 nm on a Fusion plate reader (Perkin Elmer). A dose-response curve was constructed using GraphPad Prism 4.01 (GraphPad Software Inc.) from n=2 data (from 2 individual experiments). An IC$_{50}$ value was read as the dose required to reduce the final optical density to 50% of the control value.

The IC$_{50}$ values measured for SJG-720, SJG-136 and SJG-738 were less than 10 nM.

DNA Cross-linking

Closed-circular puc18 DNA was linearized with HindIII, then dephosphorylated, and finally 5' end labeled with [γ32P]-ATP using polynucleotide kinase. Reactions containing 10 ng of DNA and drug were carried out in aqueous 1× TEOA (25 mM triethanolamine, 1 mM EDTA, pH 7.2) buffer at a final volume of 50 μL at 37° C. Reactions were terminated by addition of an equal volume of stop solution (0.6 M NaOAc, 20 mM EDTA, 100 μg/mL tRNA) followed by precipitation with ethanol. Following centrifugation of the samples, the supernatants were discarded and the pellets were dried by lyophilization. Samples were resuspended in 10 μL of alkaline denaturing buffer (4 mg bromophenol blue, 600 mg sucrose and 40 mg NaOH) and vortexed for three minutes at room temperature. The non-denatured controls were re-suspended in 10 μL of standard sucrose loading dye (2.5 mg bromophenol blue, 2.5 mg xylene cyanol blue and 4 g sucrose). Both samples and controls were loaded directly onto an agarose gel.

Electrophoresis was performed on a 0.8% submerged horizontal agarose gel, 20 cm in length for 16 hours at 38–40 V in 1× TAE running buffer (2.42 g Tris Base, 0.372 g EDTA, 0.571 ml glacial acetic acid). Gels were dried under vacuum for 80 minutes at 80° C. on a Savant SG210D SpeedGel gel dryer onto one layer of Whatman 3MM with a layer of DE81 filter paper underneath. An autoradiograph was obtained, after overnight exposure onto FujiRX x-ray film. The film bands were quantitated using a BioRad GS-670 imaging laser densitometer. The percentage of cross-linking was calculated by measuring the total DNA in each lane (the sum of the densities for the double-stranded and single-stranded bands) relative to the amount of density of double-stranded band alone. A dose response curve was derived by plotting drug concentration against the determined percentage level of cross-linked DNA, from which was derived the amount required to cross-link 50% of the DNA ($XL_{50}$).

After 2 hours the $XL_{50}$ values measured for both SJG-136 and SJG-720 were less than 500 nM.

What is claimed is:

1. A compound of formula I:

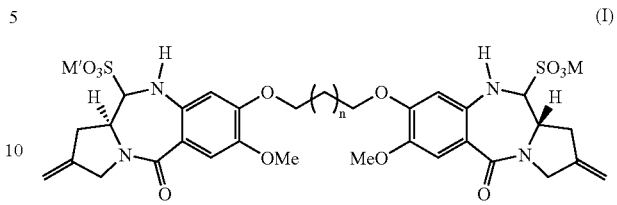

wherein n is 1 to 10, and M and M' are independently selected from monovalent pharmaceutically acceptable cations, or together represent a divalent pharmaceutically acceptable cation.

2. A compound according to claim 1, wherein n is 1, 3, 6, 7 or 8.

3. A compound according to claim 2, wherein n is 1 or 3.

4. The compound according to claim 1, wherein M and M' are the same.

5. The compound according to claim 4, wherein each of M and M' is an alkali metal ion.

6. The compound according to claim 5, wherein each of M and M' is $Na^+$.

7. The compound of claim 1, wherein the compound is purified or isolated.

8. A pharmaceutical composition comprising the compound of claim 1 and a pharmaceutically acceptable carrier.

9. A pharmaceutical composition comprising the compound of claim 2 and a pharmaceutically acceptable carrier.

10. A pharmaceutical composition comprising the compound of claim 3 and a pharmaceutically acceptable carrier.

11. A pharmaceutical composition comprising the compound of claim 4 and a pharmaceutically acceptable carrier.

12. A pharmaceutical composition comprising the compound of claim 5 and a pharmaceutically acceptable carrier.

13. A pharmaceutical composition comprising the compound of claim 6 and a pharmaceutically acceptable carrier.

14. A pharmaceutical composition comprising the compound of claim 7 and a pharmaceutically acceptable carrier.

* * * * *